US007388094B2

(12) United States Patent
Ishii et al.

(10) Patent No.: US 7,388,094 B2
(45) Date of Patent: Jun. 17, 2008

(54) PROCESSING FOR PRODUCING 2'-DEOXY-2'-FLUOROURIDINE

(75) Inventors: Akihiro Ishii, Kawagoe (JP); Takashi Ootsuka, Kawagoe (JP); Masatomi Kanai, Kawagoe (JP); Yokusu Kuriyama, Kawagoe (JP); Manabu Yasumoto, Kawagoe (JP); Kenjin Inomiya, Kawagoe (JP); Koji Ueda, Kawagoe (JP)

(73) Assignee: Central Glass Company Limited, Ube-shi (JP)

( * ) Notice: Subject to any disclaimer, the term of this patent is extended or adjusted under 35 U.S.C. 154(b) by 67 days.

(21) Appl. No.: 10/552,463

(22) PCT Filed: Apr. 9, 2004

(86) PCT No.: PCT/JP2004/005109

§ 371 (c)(1), (2), (4) Date: Oct. 7, 2005

(87) PCT Pub. No.: WO2004/089968

PCT Pub. Date: Oct. 21, 2004

(65) Prior Publication Data

US 2006/0247433 A1 Nov. 2, 2006

(30) Foreign Application Priority Data

Apr. 10, 2003 (JP) ............................ 2003-106849

(51) Int. Cl.
*C07H 19/073* (2006.01)

(52) U.S. Cl. ................................ 536/27.11; 536/28.53

(58) Field of Classification Search ... 536/27.11–28.53
See application file for complete search history.

(56) References Cited

FOREIGN PATENT DOCUMENTS

| | | |
|---|---|---|
| JP | 57-102889 | 6/1982 |
| JP | 1-272595 | 10/1989 |

OTHER PUBLICATIONS

[R] Hayakawa et al., "Diethylaminosulfur Trifluoride (DAST) as a Fluor-inating Agent of Pyrimidine Nucleotides Having a 2',3'-Vicinal Diol System," Chemical & Pharmaceutical Bulletin (Japan), 38(5), 1136-1139 (May 1990).*

Yoshiko Sato et al., "Synthesis and Hpnotic and Anti-Human Immunodeficiency Virus-1 Activities of N3-Substituted 2'-Deoxy-2'-fluorouridines", Chem.Pharm.Bull., vol. 42, 1994, pp. 595-598.

Morio Ikehara et al., "Studies on Nucleosides and Nucleotides. LXXXIX. Purine Cyclonucleosides. (43) Synthesis and Properties of 2'-Halogeno-2'-deoxyguanosines", Chem.Pharm.Bull., vol. 29, 1981, pp. 3281-3285.

Morio Ikehara et al., "Studies on Nucleosides and Nucleotides. LXXXVII. Purine Cyclonucleosides. XLII. Synthesis of 2'-deoxy-2'-fluoroguanosines", Chem.Pharm.Bull., vol. 29, 1981, pp. 1034-1038.

International Search Report dated Aug. 3, 2004 based on International Application No. PCT/JP2004/005109, filed Apr. 9, 2004.

John F. Codington, et al., "Synthesis of 2'-Fluorothymidine, 2'-Fluorodeoxyuridine, and other 2'-Halogeno-2'-Deoxy Nucleosides", Nucleosides, 1964, pp. 558-563, vol. 29, (Mar.).

R. Ranganathan, "Modification of the 2'-Position of Purine Nucleosides: Syntheses of a 2'-α-Substituted-2'Deoxyadenosine Analogs", Tetrahedron Letters, 1977, pp. 1291-1994, No. 15, Pergamon Press.

Morio Ikehara, et al., "Studies of Nucleosides and Nucleotides LXXXVI[1] Purine Cyclonucleosides 41 A New Synthesis of 2-Deoxy-2'Fluoradenosine By the Use of Tetrahydrofuranyl Protecting Group" J. Carbohydrates Nucleosides Nucleotides, (1980), pp. 131-140, vol. 7, No. 2.

* cited by examiner

*Primary Examiner*—S. Anna Jiang
*Assistant Examiner*—L. E. Crane
(74) *Attorney, Agent, or Firm*—Crowell & Moring LLP

(57) ABSTRACT

1-β-D-Arabinofuranosyluracil in 3',5'-hydroxyl-protected form is reacted with a trifluoromethanesulfonylating agent in the presence of an organic base to convert it into a 2'-triflate form, and then it is reacted with a fluorinating agent containing "a salt or complex formed by an organic base and hydrofluoric acid" to produce 2'-deoxy-2'-fluorouridine in 3',5'-hydroxyl-protected form. A deprotecting agent is further caused to act thereon to obtain 2'-deoxy-2'-fluorouridine. The 2'-deoxy-2'-fluorouridine obtained can efficiently be purified by temporarily converting it into a 3',5'-diacetyl form, recrystallizing the 3',5'-diacetyl form, and then deacetylating it. Thus, high-purity 2'-deoxy-2'-fluorouridine can be produced.

11 Claims, No Drawings

PROCESSING FOR PRODUCING 2'-DEOXY-2'-FLUOROURIDINE

This application is a 371 of PCT/JP04/05109, filed Apr. 9, 2004, an application that claims priority from Japanese Patent Office Application 2003-106,849, filed Apr. 10, 2003.

BACKGROUND OF THE INVENTION

The present invention relates to a process for producing 2'-deoxy-2'-fluorouridine, which is an important intermediate of medicines.

The target of the present invention, 2'-deoxy-2'-fluorouridine, is an important intermediate of medicines. Conventional production processes can be divided into the following two, and representative publications are cited.

(1) A process of conducting a ring opening and fluorination of 2,2'-anhydrouridine with hydrofluoric acid (see Non-patent Publication 1 (J. Org. Chem. (USA), 1964, Vol. 29, No. 3, pp. 558-564)).

(2) 1-β-D-Arabinofuranosyluracil in 3',5'-hydroxyl-protected form is dehydroxyfluorinated by DAST $((C_2H_5)_2NSF_3)$ (see Non-patent Publication 2 (Chem. Pharm. Bull. (Japan), 1994, Vol. 42, No. 3, pp. 595-598)).

As a technology related to the present invention, in syntheses of 2'-deoxy-2'-fluoroadenosine and 2'-deoxy-2'-fluoroguanosine, there are disclosed processes in which corresponding 9-β-D-arabinofuranosyladenine in 3',5'-hydroxyl-protected form and $N^2$-isobutyryl-9-β-D-arabinofuranosylguanine in 3',5'-hydroxyl-protected form are reacted with trifluoromethanesulfonyl chloride in the presence of sodium hydroxide to respectively convert them to corresponding 2'-triflates, followed by reactions with tetrabutylammonium fluoride (TBAF) (see Non-patent Publication 3 (Tetrahedron Lett. (Great Britain), 1977, Vol. 18, No. 15, pp. 1291-1294), Non-patent Publication 4 (Chem. Pharm. Bull. (Japan), 1981, Vol. 29, No. 4, pp. 1034-1038), Non-patent Publication 5 (J. Carbohyd. Nucl. Nucl. (Great Britain), 1980, Vol. 7, No. 2, pp. 131-140), Non-patent Publication 6 (Chem. Pharm. Bull. (Japan), 1981, Vol. 29, No. 11, pp. 3281-3285)).

The process for producing 2'-deoxy-2'-fluorouridine, which is disclosed in Non-patent Publication 1, was much limited in material of the reactor, since the reaction was conducted by using an excessive amount of hydrofluoric acid, which is highly corrosive, under high temperature. The productivity was inferior since the substrate was diluted with reaction solvent to high degree, and the reaction yield itself was low. From the industrial viewpoint, it was difficult to say that the process is an industrial production process, since it uses hydrofluoric acid that is difficult in handling in large amount, and since column chromatography is necessary for purifying the obtained product.

On the other hand, in the production process of non-patent publication 2, it is necessary to use a special fluorination agent that is industrially expensive and problematic in handling in large amount, and the reaction yield is also ordinary. Thus, it was difficult to say that the process is an industrial production process.

The processes for synthesizing 2'-deoxy-2'-fluoroadenosine or 2'-deoxy-2'-fluoroguanosine, which are disclosed in Non-patent Publications 3-6, gave the target with only very low yield.

The reaction of obtaining 2'-deoxy-2'-fluoroadenosine or 2'-deoxy-2'-fluoroguanosine by fluorinating a 2'-triflate form, which is disclosed in Non-patent Publications 3-6, is considered to be a nucleophilic $S_N2$ substitution reaction by fluorine anion (F$^-$). In this reaction, "an elimination reaction of a triflate group ($CF_3SO_3^-$ group)" occurs competitively as a side reaction, and there is produced as a by-product a compound in which 1'-position carbon and 2'-position carbon are bonded by a double bond. The cause of low yield in the Non-patent Publication 3 is also due to this side reaction. This is an essential problem inherent in the nucleophilic $S_N2$ substitution reaction by fluorine anion (F$^-$). A similar problem arises in the production of the present invention's target compound 2'-deoxy-2'-fluorouridine, too.

Thus, there was a strong desire for a process of industrially advantageously producing 2'-deoxy-2'-fluorouridine.

Furthermore, since 2'-deoxy-2'-fluorouridine, the final target compound in the present invention, is a water-soluble and scarcely crystalline compound, it was necessary to conduct a purification by column chromatography to purify it as a high-purity, white-color, crystalline powder with high recovery (Non-patent Publication 1 and Non-patent Publication 2). Thus, it placed a burden in purification procedure. There has been no report yet of a process capable of purifying it in the form of a high-purity, white-color, crystalline powder with high recovery by a simple purification procedure like recrystallization purification. Thus, there was also a strong desire for an industrial purification process of 2'-deoxy-2'-fluorouridine.

SUMMARY OF THE INVENTION

It is an object of the present invention to provide an industrial production process of 2'-deoxy-2'-fluorouridine, which is an important intermediate of medicines.

It is another object of the present invention to provide an industrial production process of 2'-deoxy-2'-fluorouridine in 3',5'-hydroxyl-protected form, which is a precursor of 2'-deoxy-2'-fluorouridine.

The present invention provides a first process for producing 2'-deoxy-2'-fluorouridine in 3',5'-hydroxyl-protected form represented by the formula [4],

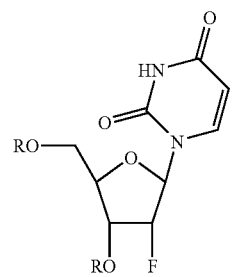

[4]

[in the formula, R represents a protecting group of hydroxyl group] by reacting 1-β-D-arabinofuranosyluracil in 3',5'-hydroxyl-protected form represented by the formula [1],

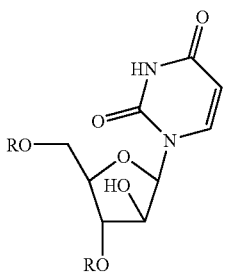

[1]

[in the formula, R represents a protecting group of hydroxyl group] with a trifluoromethanesulfonylating agent represented by the formula [2], $$CF_3SO_2X \quad [2]$$

[in the formula, X represents a F atom, Cl atom or $CF_3SO_3$ group] in the presence of an organic base, to convert it to a 2'-triflate form represented by the formula [3],

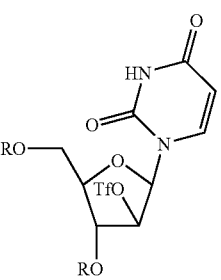

[3]

[in the formula, R represents a protecting group of hydroxyl group, and Tf represents a $CF_3SO_2$ group], followed by reacting with a fluorinating agent comprising "a salt or complex comprising an organic base and hydrofluoric acid".

The first process may be a second process. The second process is the same as the first process except in that the above trifluoromethanesulfonylating agent represented by the formula [2] is a trifluoromethanesulfonylating agent represented by the formula [5].

$$CF_3SO_2F \quad [5]$$

Furthermore, the above first process may be a third process. In the third process, 2'-deoxy-2'-fluorouridine in 3',5'-hydroxyl-protected form represented by the formula [8]

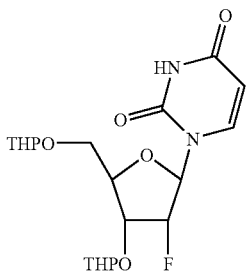

[8]

[in the formula, THP represents a tetrahydropyranyl group] is produced by reacting 1-β-D-arabinofuranosyluracil in 3',5'-hydroxyl-protected form represented by the formula [6],

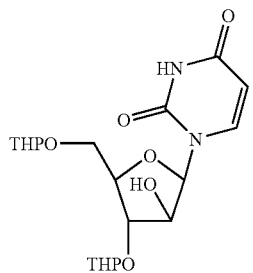

[6]

[in the formula, THP represents a tetrahydropyranyl group] with a trifluoromethanesulfonylating agent represented by the formula [5], $$CF_3SO_2F \quad [5]$$

in the presence of triethylamine, to convert it to a 2'-triflate form represented by the formula [7],

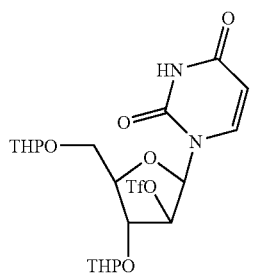

[7]

[in the formula, THP represents a tetrahydropyranyl group, and Tf represents a $CF_3SO_2$ group], followed by reacting with a fluorinating agent comprising "a salt or complex comprising triethylamine and hydrofluoric acid".

Furthermore, the present invention provides a fourth process for producing 2'-deoxy-2'-fluorouridine represented by the formula [9],

[9]

by reacting 2'-deoxy-2'-fluorouridine in 3',5'-hydroxyl-protected form represented by the formula [4],

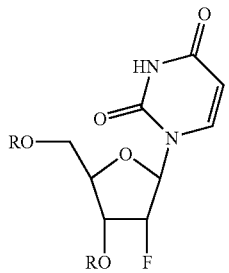

[4]

[in the formula, R represents a protecting group of hydroxyl group] or 2'-deoxy-2'-fluorouridine in 3',5'-hydroxyl-protected form represented by the formula [8],

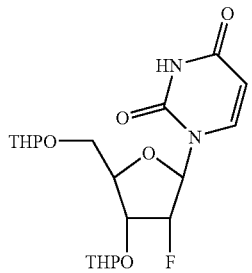

[8]

which has been produced by any one of the above first to third processes, with a deprotecting agent.

Furthermore, the present invention provides a fifth process for purifying 2'-deoxy-2'-fluorouridine represented by the formula [9],

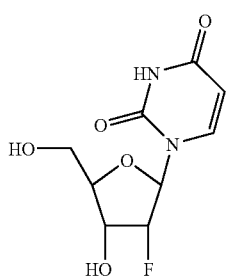

[9]

comprising reacting 2'-deoxy-2'-fluorouridine represented by the formula [9],

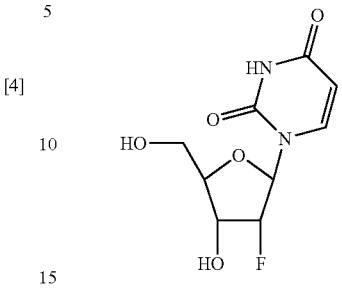

[9]

with an acetylating agent in the presence of an organic base, to convert it to 2'-deoxy-2'-fluorouridine in 3',5'-diacetylated form represented by the formula [10],

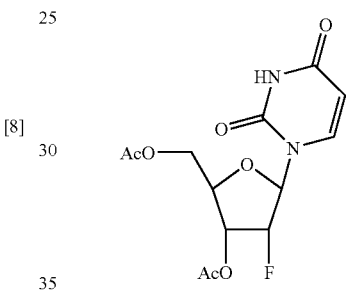

[10]

[in the formula, Ac represents an acetyl group], followed by a recrystallization purification of the 2'-deoxy-2'-fluorouridine in 3',5'-diacetylated form and then reacting with a deacetylating agent.

The fifth process may be a sixth process. The sixth process is the same as the fifth process except in that 2'-deoxy-2'-fluorouridine represented by the formula [9] is one produced by the fourth process.

DETAILED DESCRIPTION

As a result of an eager examination by the present inventors to solve the above task, we have made it clear that, in the case of using 1-β-D-arabinofuranosyluracil in 3',5'-hydroxyl-protected form, which is a target in the present invention, is used as a substrate, the target trifluoromethanesulfonylation at 2'-position and the subsequent nucleophilic $S_N2$ substitution reaction by fluorine anion ($F^-$) at 2'-position proceed well under specific conditions.

A particularly important point of the present invention resides in using "a salt or complex comprising an organic base and hydrofluoric acid" as a fluorinating agent in the fluorination step of 2'-triflate form.

As mentioned above, an elimination reaction of the triflate group ($CF_3SO_3^-$ group) competes as a side reaction in the nucleophilic $S_N2$ substitution reaction by fluorine anion ($F^-$). The present inventors, however, have made it clear that this elimination reaction can be highly suppressed by replacing tetrabutylammonium fluoride (TBAF), which is a strongly basic fluorinating agent used in the above Non-patent Publications 3-6, with "a salt or complex comprising an organic base and hydrofluoric acid", which is a fluorinating agent that is relatively high in nucleophilicity of fluorine anion ($F^-$) and is weak in basicity.

Furthermore, the present inventors have found that "a salt or complex comprising pyridine or triethylamine and hydrofluoric acid" is particularly preferable as this fluorination agent.

In particular, we have made it clear that "a complex (($C_2H_5)_3N.3HF$) comprising 1 mol of triethylamine and 3 mols of hydrofluoric acid" and "a complex (trade name: ~10 mol % $C_5H_5N$. ~90 mol % HF) comprising about 30% (about 10 mol %) of pyridine and about 70% (about 90 mol %) of hydrofluoric acid", which are sold on the market industrially with low prices and are relatively safe in handling, can preferably be used.

In particular, a complex (($C_2H_5)_3N.3HF$) comprising 1 mol of triethylamine and 3 mols of hydrofluoric acid does not cause problems such as devitrification and corrosion, even if glass reaction vessel is used. Therefore, it is particularly advantageous from the point of reaction vessel material, too.

In syntheses of 2'-deoxy-2'-fluoroadenosine and 2'-deoxy-2'-fluoroguanosine in conventional techniques (Non-patent Publications 3-6), tetrabutylammonium fluoride (TBAF) was used as a fluorinating agent in each of them. In this case, it is generally difficult to selectively remove TBAF used excessively and tetrabutylammonium hydroxide (($n$-Bu)$_4$NOH) produced by a post-treatment operation with water, from the product. However, in the case of using the above fluorinating agent, it was possible to selectively remove from the product the fluorinating agent used excessively, by a simple purification operation such as washing with water, thereby achieving a great improvement of operability upon industrial production.

Furthermore, there was obtained in the present invention a new finding relating to protecting groups of hydroxyl groups at 3'-position and 5'-position in the production of 2'-deoxy-2'-fluorouridine.

There is disclosed that tetrahydrofuranyl group (THF group) is superior as protecting groups of hydroxyl groups at 3'-position and 5'-position to tetrahydropyranyl group (THP group) in deprotecting steps in the syntheses of 2'-deoxy-2'-fluoroadenosine and 2'-deoxy-2'-fluoroguanosine (Non-patent Publication 4 and Non-patent Publication 5). However, 2,3-dihydrofurane, which is a protecting agent of tetrahydrofuranyl group (THF group), has a lower boiling point (54° C.) as compared with that (86° C.) of 3,4-dihydro-2H-pyrane, which is a protecting agent of tetrahydropyranyl group. Therefore, its handling is difficult, and it has a high price industrially.

However, it was made clear in the production of 2'-deoxy-2'-fluorouridine, which is a target in the present invention, that the deprotecting step proceeds well, even if the protecting groups of hydroxyl groups at 3'-position and 5'-position are tetrahydropyranyl groups (THP groups).

"A 2'-triflate form of which hydroxyl groups at 3'-position and 5'-position are protected with tetrahydropyranyl groups (THP groups)", which is produced as an intermediate in the case of using this THP group as a protecting group, is a novel compound and is a preferable intermediate in an industrial production process of 2'-deoxy-2'-fluorouridine.

Furthermore, it was made clear in the present invention that trifluoromethanesulfonylfluoride ($CF_3SO_2F$) can preferably be used in a trifluoromethanesulfonylation reaction of 2'-position hydroxyl group of 1-β-D-arabinofuranosyluracil in 3',5'-hydroxyl-protected form.

The reaction proceeds even if trifluoromethanesulfonic acid anhydride (($CF_3SO_2)_2O$) is used as a trifluoromethanesulfonylating agent to 2'-position hydroxyl group. Although trifluoromethanesulfonic acid anhydride (($CF_3SO_2)_2O$) has two trifluoromethanesulfonyl groups ($CF_3SO_2$ groups), one is used in the reaction, and the rest acts as a leaving group in the form of triflate group ($CF_3SO_3^-$ group). Therefore, the use of trifluoromethanesulfonic acid anhydride (($CF_3SO_2)_2O$) is not necessarily efficient from the viewpoint of atom economy.

Although the reaction proceeds even by using trifluoromethanesulfonyl chloride ($CF_3SO_2Cl$), there is disclosed (Non-patent Publication 6) that, in the synthesis of 2'-deoxy-2'-fluoroguanosine, chlorine anion ($Cl^-$) produced as a by-product with the progress of the reaction subsequently causes a substitution reaction in the reaction system with the 2'-triflate form as the product to give a by-product in which chlorine atom has been substituted therefore at 2'-position. Since nucleophilicity of chlorine anion ($Cl^-$) is greatly higher than that of fluorine anion ($F^-$), it becomes a significant side reaction. Therefore, the use of trifluoromethanesulfonyl chloride ($CF_3SO_2Cl$) is also limited.

A process for industrially producing a series of trifluoromethanesulfonic acid derivatives is shown in Scheme 1. In this flow, since trifluoromethanesulfonyl fluoride ($CF_3SO_2F$) is at a further upstream position, it is industrially the most advantageous to use trifluoromethanesulfonyl fluoride ($CF_3SO_2F$).

As a result of an eager examination in view of such background, it was found that the reaction proceeds well even by using trifluoromethanesulfonyl fluoride ($CF_3SO_2F$) in trifluoromethanesulfonylation of 1-β-D-arabinofuranosyluracil in 3',5'-hydroxyl-protected form, which is the target of the present invention. As a result of this, it became possible to essentially avoid the above problems, that is, (1) lowness in utilization factor of trifluoromethanesulfonyl group ($CF_3SO_2$ group) and (2) by-production of a compound in which chlorine atom has been substituted therefore at 2'-position. Although it is necessary to make a base coexistent in this trifluoromethanesulfonylating reaction, it is not necessary to use sodium hydride, which is industrially high in price and is inflammable, as the base. It is possible to use an organic base, such as pyridine and triethylamine, which are industrially low in price and are easy in handling.

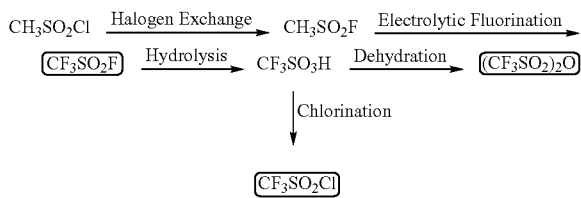

Scheme 1

Furthermore, the present inventors have found a new process for purifying the obtained 2'-deoxy-2'-fluorouridine. That is, we have noticed easy crystallinity of 2'-deoxy-2'-fluorouridine in 3',5'-diacetylated form. We have made it clear that 2'-deoxy-2'-fluorouridine of high purity can be obtained through a purification by once turning a low-purity product of 2'-deoxy-2'-fluorouridine into a 3',5'-diacetylated form, by subjecting this 3',5'-diacetylated form to recrystallization purification to increase purity, and by conducting a deacetylation again. The thus obtained 2'-deoxy-2'-fluorouridine does not become amorphous and can be recovered with good yield as a white-color crystalline powder of high purity. Thus, we have made it clear that 2'-deoxy-2'-fluorouridine is obtained as a white-color crystalline powder of high purity, while avoiding a purification process of burden such as purification by column chromatography.

Finally, since each reaction step in the production process of the present invention is high in selectivity and does almost not produce by-products that are difficult in separation, it is possible to conduct the trifluoromethanesulfonylation step of the first step and the fluorination step of the second step in a one-pot reaction, and it is also possible to conduct the deprotecting step of the third step and the acetylation step of the fourth step. Thus, it is an extremely useful process for industrially producing 2'-deoxy-2'-fluorouridine.

In the following, a process for producing 2'-deoxy-2'-fluorouridine of the present invention is explained in detail. As shown in Scheme 2, the present invention comprises the six production steps of (1) trifluoromethanesulfonylation step, (2) fluorination step, (3) deprotection step, (4) acetylation step, (5) recrystallization purification step, and (6) deacetylation.

group) are preferable. In particular, tetrahydropyranyl group (THP group) is more preferable. The compound represented by the formula [1] can be produced, based on Non-patent Publication 2 and Khim. Geterotsikl. Soedin. (Russia), 1996, No. 7, p. 975-977. According to these publications, it is possible to obtain one in which 3'-position and 5'-position are selectively protected.

As the trifluoromethanesulfonylating agent represented by the formula [2], trifluoromethanesulfonyl fluoride ($CF_3SO_2F$), trifluoromethanesulfonyl chloride ($CF_3SO_2Cl$), and trifluoromethanesulfonic acid anhydride (($CF_3SO_2)_2O$) are cited. Of them, trifluoromethanesulfonyl fluoride ($CF_3SO_2F$) and trifluoromethanesulfonic acid anhydride (($CF_3SO_2)_2O$) are preferable. In particular, trifluoromethanesulfonyl fluoride ($CF_3SO_2F$) is more preferable.

Regarding the amount of the trifluoromethanesulfonylating agent represented by the formula [2] to be used, it may be used in 1 mol or greater, generally preferably 1-20 moles, particularly more preferably 1-10 moles, relative to 1 mol of the 1-β-D-arabinofuranosyluracil in 3',5'-hydroxyl-protected form represented by the formula [1].

As the organic base, trimethylamine, triethylamine, diisopropylethylamine, tri-n-butylamine, dimethyllaurylamine, 4-dimethylaminopyridine, N,N-dimethylaniline, dimethylbenzylamine, 1,5-diazabicyclo[4,3,0]non-5-ene, 1,8-diazabicyclo[5,4,0]undec-7-ene, 1,4-diazabicyclo[2,2,2]octane, pyridine, 2,4-lutidine, 2,5-lutidine, 2,6-lutidine, 3,4-lutidine, Scheme 2

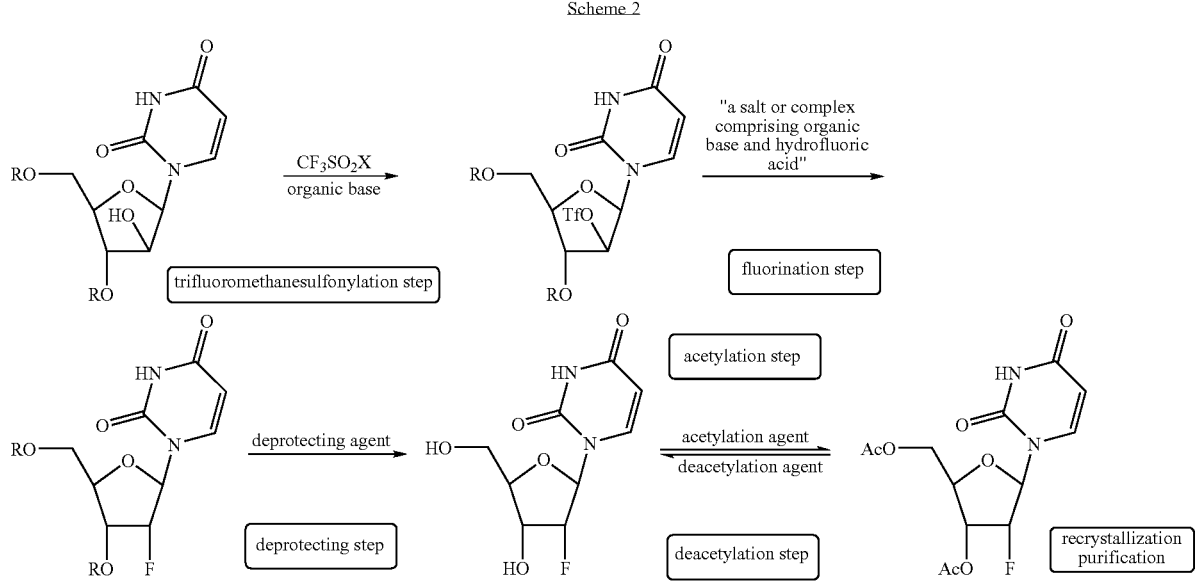

Firstly, the trifluoromethanesulfonylation step of the first step is explained in detail. The trifluoromethanesulfonylation step of the first step is achieved by reacting 1-β-D-arabinofuranosyluracil in 3',5'-hydroxyl-protected form represented by the formula [1] with a trifluoromethanesulfonylating agent represented by the formula [2] in the presence of an organic base.

As R of 1-β-D-arabinofuranosyluracil in 3',5'-hydroxyl-protected form represented by the formula [1], which is the starting material, trityl group (triphenylmethyl group), tetrahydropyranyl group (THP group), tetrahydrofuranyl group (THF group) and the like are cited. Of them, tetrahydropyranyl group (THP group) and tetrahydrofuranyl group (THF 3,5-lutidine, 2,4,6-trimethylpyridine, imidazole, pyrimidine, and pyridazine and the like are cited. Of them, triethylamine and pyridine are preferable. In particular, triethylamine is more preferable.

Regarding the amount of the organic base to be used, it may be used generally in 1 mol or greater, preferably 2-20 mols, particularly more preferably 3-10 mols, relative to 1 mol of the 1-β-D-arabinofuranosyluracil in 3',5'-hydroxyl-protected form represented by the formula [1].

Although it is possible to conduct the reaction even if reaction solvent is not used in particular, its use is preferable. As such reaction solvent, there are cited aliphatic hydrocarbons such as n-pentane, n-hexane, cyclohexane, and n-heptane; aromatic hydrocarbons such as benzene, toluene, ethylbenzene, xylene, and mesitylene; halogenated hydrocarbons such as methylene chloride, chloroform, and 1,2-dichloroethane; ethers such as diethyl ether, tetrahydrofuran, t-butyl methyl ether, and 1,4-dioxane; esters such as ethyl acetate and n-butyl acetate; amides such as hexamethylphosphoric acid triamide, N,N-dimethylformamide, N,N-dimethylacetamide, and N-methylpyrollidone; nitriles such as acetonitrile and propionitrile; and dimethylsulfoxide. Of them, toluene, methylene chloride, tetrahydrofuran, ethyl acetate, N,N-dimethylformamide, N,N-dimethylacetoamide, acetonitrile and dimethylsulfoxide are preferable. In particular, methylene chloride, N,N-dimethylformamide and acetonitrile are more preferable. It is possible to use these reaction solvents alone or in combination.

Regarding the amount of the reaction solvent to be used, it may be used in 0.1 L or greater, preferably 0.1-20 L, particularly more preferably 0.1-10 L, relative to 1 mol of the 1-β-D-arabinofuranosyluracil in 3',5'-hydroxyl-protected form represented by the formula [1].

The temperature condition is generally −100 to +50° C., preferably −80 to +20° C., particularly more preferably −60 to −10° C. In case that the reaction is conducted by using trifluoromethanesulfonyl fluoride ($CF_3SO_2F$) of the trifluoromethanesulfonylating agent represented by the formula [2], under a temperature condition of the boiling point (−21° C.) or higher, it is possible to use a pressure-proof reaction vessel.

Although the reaction time is generally 0.1-24 hr, it varies depending on the type of the substrate and the reaction conditions. Therefore, it is preferable to consider the time when the raw material has almost been consumed, as the end point, by tracing the progress condition of the reaction by an analytical means such as gas chromatography, liquid chromatography, and NMR.

The post-treatment is not particularly limited. In general, it is possible to obtain a crude product by adding water, sodium hydrogencarbonate aqueous solution or brine or the like to the reaction-terminated liquid, followed by extraction with an organic solvent such as toluene, methylene chloride, or ethyl acetate, then washing the recovered organic layer with water or brine or the like, drying with a drying agent such as anhydrous sodium sulfate or anhydrous magnesium sulfate, filtration, concentration, and vacuum drying. According to need, it is possible to obtain the target 2'-triflate form represented by the formula [3] with high chemical purity by subjecting the crude product to a purification operation such as activated carbon treatment or recrystallization. However, since the 2'-triflate form is high in reactivity, it is effective to conduct the trifluoromethansulfonylating step of the first step and the fluorination step of the second step as a one-pot reaction by directly adding a fluorinating agent comprising "a salt or complex comprising an organic base and hydrofluoric acid" to the reaction-terminated liquid, without conducting the post-treatment operation and isolation to the outside of the system. Furthermore, it is also effective to conduct the trifluoromethansulfonylating step of the first step and the fluorination step of the second step as a one-pot reaction by adding the trifluoromethanesulfonylating agent represented by the formula [2] in the presence of an organic base and a fluorinating agent comprising "a salt or complex comprising an organic base and hydrofluoric acid". In the case of using trifluoromethanesulfonyl fluoride ($CF_3SO_2F$) as the trifluoromethanesulfonylating agent represented by the formula [2], although "a salt or complex comprising an organic base and hydrofluoric acid" is produced as a by-product as the reaction proceeds, the subsequent fluorination reaction does almost not proceed. Therefore, it is necessary to newly add a fluorinating agent comprising "a salt or complex comprising an organic base and hydrofluoric acid".

Next, the fluorination step of the second step is explained in detail. The fluorination step of the second step is achieved by reacting the 2'-triflate form represented by the formula [3] with a fluorination agent comprising "a salt or complex comprising an organic base and hydrofluoric acid".

As the organic base in the fluorinating agent comprising "a salt or complex comprising an organic base and hydrofluoric acid", there are cited trimethylamine, triethylamine, diisopropylethylamine, tri-n-butylamine, dimethyllaurylamine, 4-dimethylaminopyridine, N,N-dimethylaniline, dimethylbenzylamine, 1,5-diazabicyclo[4,3,0]non-5-ene, 1,8-diazabicyclo[5,4,0]undec-7-ene, 1,4-diazabicyclo[2,2,2]octane, pyridine, 2,4-lutidine, 2,5-lutidine, 2,6-lutidine, 3,4-lutidine, 3,5-lutidine, 2,4,6-trimethylpyridine, imidazole, pyrimidine, pyridazine, and the like. Of them, triethylamine and pyridine are preferable. In particular, triethylamine is more preferable.

The molar ratio of the organic base to the hydrofluoric acid in the fluorinating agent is generally in a range of 100:1 to 1:100, preferably in a range of 50:1 to 1:50, particularly more preferably in a range of 25:1 to 1:25. Furthermore, it is extremely convenient to use "a complex (($C_2H_5)_3$N.3HF) comprising 1 mol of triethylamine and 3 mols of hydrofluoric acid" and "a complex (trade name: ~10 mol % $C_5H_5$N. ~90 mol % HF) comprising about 30% (about 10 mol %) of pyridine and about 70% (about 90 mol %) of hydrofluoric acid", which are commercially sold by Aldrich (Aldrich, 2003-2004 General Catalogue).

The amount of the fluorinating agent comprising "a salt or complex comprising an organic base and hydrofluoric acid" may be used in generally 1 mol or greater, preferably 1-20 mols, particularly more preferably 1-10 mols, relative to 1 mol of the 2'-triflate form represented by the formula [3].

Although it is possible to conduct the reaction even if reaction solvent is not used in particular, its use is preferable. As such reaction solvent, there are cited aliphatic hydrocarbons such as n-pentane, n-hexane, cyclohexane, and n-heptane; aromatic hydrocarbons such as benzene, toluene, ethylbenzene, xylene, and mesitylene; halogenated hydrocarbons such as methylene chloride, chloroform, and 1,2-dichloroethane; ethers such as diethyl ether, tetrahydrofuran, t-butyl methyl ether, and 1,4-dioxane; esters such as ethyl acetate and n-butyl acetate; amides such as hexamethylphosphoric acid triamide, N,N-dimethylformamide, N,N-dimethylacetamide, and N-methylpyrollidone; nitriles such as acetonitrile and propionitrile; and dimethylsulfoxide. Of them, toluene, methylene chloride, tetrahydrofuran, ethyl acetate, N,N-dimethylformamide, N,N-dimethylacetoamide, acetonitrile and dimethylsulfoxide are preferable. In particular, methylene chloride, N,N-dimethylformamide and acetonitrile are more preferable. It is possible to use these reaction solvents alone or in combination.

Regarding the amount of the reaction solvent to be used, it may be used in 0.1 L or greater, preferably 0.1-20 L, particularly more preferably 0.1-10 L, relative to 1 mol of the triflate form represented by the formula [3].

The temperature condition is generally −100 to +100° C., preferably −80 to +80° C., particularly more preferably −60 to +60° C.

Although the reaction time is generally 0.1-120 hr, it varies depending on the type of the substrate and the reaction conditions. Therefore, it is preferable to terminate the reaction after confirming that the raw material has almost been consumed by tracing the progress condition of the reaction by an analytical means such as gas chromatography, liquid chromatography, and NMR.

The post-treatment is not particularly limited. In general, it is possible to obtain a crude product by adding water, sodium hydrogencarbonate aqueous solution, potassium carbonate aqueous solution or brine or the like to the reaction-terminated liquid, followed by extraction with an organic solvent such as toluene, methylene chloride, or ethyl acetate or the like, then washing the recovered organic layer with water or brine or the like, drying with a drying agent such as anhydrous sodium sulfate or anhydrous magnesium sulfate or the like, filtration, concentration, and vacuum drying. According to need, it is possible to obtain the target 2'-deoxy-2'-fluorouridine in 3',5'-hydroxyl-protected form represented by the formula [4] with high chemical purity by subjecting the crude product to a purification operation such as activated carbon treatment or recrystallization.

Next, the deprotecting step of the third step is explained in detail. The deprotecting step of the third step is achieved by reacting the 2'-deoxy-2'-fluorouridine in 3',5'-hydroxyl-protected form obtained by the second step, with a deprotecting agent.

In the deprotecting reaction, it is preferable to use an acid catalyst for the deprotecting agent. It is preferably conducted in a reaction solvent of alcohol.

As the acid catalyst, there are cited organic acids such as formic acid, acetic acid, propionic acid, trifluoroacetic acid, methanesulfonic acid, trifluoromethanesulfonic acid, benzensulfonic acid, p-toluenesulfonic acid, PPTS (pyridinium p-toluenesulfonate), and 10-camphorsulfonic acid; ion exchange resins such as Amberlyst H-15, Dowex 50W-X8; and inorganic acids such as hydrochloric acid, hydrobromic acid, sulfuric acid and phosphoric acid. Of them, acetic acid, p-toluenesulfonic acid, hydrochloric acid and sulfuric acid are preferable. In particular, p-toluenesulfonic acid and sulfuric acid are more preferable.

The amount of the acid catalyst may be used in catalytic amount or more, preferably 0.01 to 100 moles, particularly more preferably 0.03-50 moles, generally relative to 2'-deoxy-2'-fluorouridine in 3',5'-hydroxyl-protected form represented by the formula [4].

As the reaction solvent, it is preferable to use an alcoholic reaction solvent. As such solvent, there are cited methanol, ethanol, n-propanol, i-propanol, n-butanol, i-butanol, sec-butanol, tert-butanol and the like. Of them, methanol, ethanol, n-propanol and n-butanol are preferable. In particular, methanol, ethanol and n-propanol are more preferable. These reaction solvents can be used alone or in combination.

Regarding the amount of the reaction solvent to be used, it may be used in 0.1 L or greater, preferably 0.1-20 L, particularly more preferably 0.1-10 L, relative to 1 mol of the 2'-deoxy-2'-fluorouridine in 3',5'-hydroxyl-protected form represented by the formula [4].

The temperature condition is generally −20 to +100° C., preferably −10 to +80° C., particularly more preferably 0 to +60° C.

Although the reaction time is generally 0.1-48 hr, it varies depending on the type of the substrate and the reaction conditions. Therefore, it is preferable to terminate the reaction after confirming that the raw material has almost been consumed by tracing the progress condition of the reaction by an analytical means such as thin-layer chromatography, liquid chromatography, and NMR.

The post-treatment is not particularly limited. In general, it is possible to obtain a crude product of the target 2'-deoxy-2'-fluorouridine represented by the formula [9] by adding an organic base or inorganic base, followed by concentrating the alcoholic reaction solvent. The acetylation reaction of the fourth step proceeds sufficiently well by reacting the present crude product with the acetylating agent.

Next, the acetylation step of the fourth step is explained in detail. The acetylation step of the fourth step is achieved by reacting 2'-deoxy-2'-fluorouridine represented by the formula [9] with an acetylating agent in the presence of organic base.

As the acetylating agent, there are cited anhydrous acetic acid, acetyl fluoride, acetyl chloride, acetyl bromide, and the like. Of them, anhydrous acetic acid, acetyl chloride and acetyl bromide are preferable. In particular, anhydrous acetic acid and acetyl chloride are more preferable.

The amount of the acetylating agent may be generally 2 mols or greater, preferably 2-20 mols, particularly preferably 2-10 mols, relative to 1 mol of 2'-deoxy-2'-fluorouridine represented by the formula [9].

As the organic base, there are trimethylamine, triethylamine, diisopropylethylamine, tri-n-butylamine, dimethyllaurylamine, 4-dimethylaminopyridine, N,N-dimethylaniline, dimethylbenzylamine, 1,5-diazabicyclo[4,3,0]non-5-ene, 1,8-diazabicyclo[5,4,0]undec-7-ene, 1,4-diazabicyclo[2,2,2]octane, pyridine, 2,4-lutidine, 2,5-lutidine, 2,6-lutidine, 3,4-lutidine, 3,5-lutidine, 2,4,6-trimethylpyridine, imidazole, pyrimidine, and pyridazine and the like are cited. Of them, triethylamine and pyridine are preferable. In particular, pyridine is more preferable.

The amount of the organic base may be used in generally 2 mols or greater, preferably 2-20 mols, particularly more preferably 2-10 moles, relative to 1 mol of 2'-deoxy-2'-fluorouridine represented by the formula [9].

As the reaction solvent, there are cited aliphatic hydrocarbons such as n-pentane, n-hexane, cyclohexane, and n-heptane; aromatic hydrocarbons such as benzene, toluene, ethylbenzene, xylene, and mesitylene; halogenated hydrocarbons such as methylene chloride, chloroform, and 1,2-dichloroethane; ethers such as diethyl ether, tetrahydrofuran, t-butyl methyl ether, and 1,4-dioxane; esters such as ethyl acetate and n-butyl acetate; amides such as hexamethylphosphoric acid triamide, N,N-dimethylformamide, N,N-dimethylacetamide, and N-methylpyrollidone; nitriles such as acetonitrile and propionitrile; and dimethylsulfoxide. Of them, toluene, methylene chloride, tetrahydrofuran, ethyl acetate, N,N-dimethylformamide, N,N-dimethylacetoamide, acetonitrile and dimethylsulfoxide are preferable. In particular, methylene chloride and N,N-dimethylformamide are more preferable. It is possible to use these reaction solvents alone or in combination. The use of excessive amounts of the acetylating agent and the organic base can serve as the reaction solvent, too.

The temperature condition is generally −20 to +100° C., preferably −10 to +80° C., particularly more preferably 0 to +60° C.

Although the reaction time is generally 0.1-48 hr, it varies depending on the reaction conditions. Therefore, it is preferable to consider the time when the raw material has almost been consumed, as the end point, by tracing the progress condition of the reaction by an analytical means such as gas chromatography, liquid chromatography, and NMR.

The post-treatment is not particularly limited. In general, it is possible to obtain crude crystals of the target 2'-deoxy-2'-fluorouridine in 3',5'-diacetylated form represented by the formula [10] by concentrating the acetylating agent and the organic base in the reaction-terminated liquid, which have been used excessively, and the reaction solvent, followed by adding water to the concentration residue, filtration of the precipitated crystals, washing with water or an organic solvent such as toluene, methylene chloride or ethyl acetate, and vacuum drying.

Next, the recrystallization purification step of the fifth step is explained in detail. The recrystallization purification step of the fifth step is achieved by subjecting crude crystals of 2'-deoxy-2'-fluorouridine in 3',5'-diacetylated form represented by the formula [10] obtained by the fourth step to a recrystallization purification.

As the recrystallization solvent, there are cited aliphatic hydrocarbons such as n-pentane, n-hexane, cyclohexane, and n-heptane; aromatic hydrocarbons such as benzene, toluene, ethylbenzene, xylene, and mesitylene; halogenated hydrocarbons such as methylene chloride, chloroform, and 1,2-dichloroethane; ethers such as diethyl ether, tetrahydrofuran, t-butyl methyl ether, and 1,4-dioxane; ketones such as acetone, methyl ethyl ketone, and methyl i-butyl ketone; esters such as ethyl acetate and n-butyl acetate; nitriles such as acetonitrile and propionitrile; alcohols such as methanol, ethanol, n-propanol, i-propanol, n-butanol, and i-butanol; water; and the like. Of them, n-hexane, n-heptane, methylene chloride, tetrahydrofuran, acetone, methyl ethyl ketone, ethyl acetate, acetonitrile, methanol, ethanol, n-propanol, i-propanol and water are preferable. In particular, n-heptane, acetone, acetonitrile, methanol, ethanol, n-propanol, i-propanol and water are more preferable. These recrystallization solvents can be used alone or in combination.

The amount of the recrystallization solvent may be generally in 1 ml or greater, preferably 1-100 ml, particularly preferably 1-50 ml, relative to 1 g of the crude crystals of 2'-deoxy-2'-fluorouridine represented by the formula [10].

In the present recrystallization purification, it is possible to precipitate crystals smoothly and efficiently by adding seed crystals. The amount of the seed crystals may be used generally in 0.0001 g or greater, preferably 0.0001-0.1 g, particularly more preferably 0.001-0.05 g.

The temperature condition can appropriately be set by boiling point and freezing point of the recrystallization solvent to be used. In general, the crude crystals prior to purification are dissolved at a temperature of from 30° C. to the vicinity of boiling point of the recrystallization solvent. Then, under standing still or under stirring, crystals are precipitated while the temperature is lowered. Finally, it is cooled down to −20° C. to room temperature (25° C.).

In the present recrystallization purification, the precipitated crystals are improved in chemical purity. Therefore, it is possible to obtain 2'-deoxy-2'-fluorouridine in 3',5'-deacetylated form represented by the formula [10] of high chemical purity by recovering the precipitated crystals by filtration or the like. By repeating the present recrystallization operation, it is possible to obtain one of higher chemical purity. Decolorizing is also possible by subjecting a solution prepared by dissolving the crude crystals prior to purification in the recrystallization solvent, to an activated carbon treatment.

Although the purification time is generally 0.1-120 hours, it varies depending on the purification conditions. Therefore, it is preferable to consider the time when the recovery was possible with high chemical purity and good yield by a monitor analysis of the precipitated crystal chemical purity and the amount of the precipitated crystals, as the end point.

Finally, the deacetylation step of the sixth step is described in detail. The deacetylation step of the sixth step is achieved by reacting 2'-deoxy-2'-fluorouridine in 3',5'-deacetylated form represented by the formula [10] of high chemical purity with a deacetylating agent.

It is preferable to use an acid catalyst or base as the deacetylating agent in the deacetylation reaction, and it is conducted preferably in an alcoholic reaction solvent.

As the acid catalyst, there are cited organic acids such as formic acid, acetic acid, propionic acid, trifluoroacetic acid, methanesulfonic acid, trifluoromethanesulfonic acid, benzensulfonic acid, p-toluenesulfonic acid, PPTS (pyridinium p-toluenesulfonate), and 10-camphorsulfonic acid; ion exchange resins such as Amberlyst H-15, Dowex 50W-X8; and inorganic acids such as hydrochloric acid, hydrobromic acid, sulfuric acid and phosphoric acid. Of them, acetic acid, p-toluenesulfonic acid, hydrochloric acid and sulfuric acid are preferable. In particular, p-toluenesulfonic acid and hydrochloric acid are more preferable.

The amount of the acid catalyst may be used in catalytic amount or more, generally preferably 0.01-100 moles, particularly more preferably 0.03-50 moles.

As the base, there are cited lower alkyl primary amines of 1-6 in carbon number, such as methylamine, ethylamine, n-propylamine, i-propylamine, n-butylamine, sec-butylamine, tert-butylamine, n-pentylamine, n-hexylamine, and cyclohexylamine, ammonia, and the like. Of them, methylamine, ethylamine, n-propylamine, n-butylamine and ammonia are preferable. In particular, methylamine, ethylamine and ammonia are more preferable.

The amount of the base may be used generally in 2 moles or greater, preferably 2-200 moles, particularly more preferably 2-100 moles, relative to 1 mol of 2'-deoxy-2'-fluorouridine in 3',5'-deacetylated form of high purity represented by the formula [10].

As the reaction solvent, it is preferable to use an alcoholic reaction solvent. As such solvent, there are cited methanol, ethanol, n-propanol, i-propanol, n-butanol, i-butanol, sec-butanol, tert-butanol and the like. Of them, methanol, ethanol, n-propanol and n-butanol are preferable. In particular, methanol, ethanol and n-propanol are more preferable. These reaction solvents can be used alone or in combination.

Regarding the amount of the reaction solvent to be used, it may be used in 0.1 L or greater, preferably 0.1-20 L, particularly more preferably 0.1-10 L, relative to relative to 1 mol of 2'-deoxy-2'-fluorouridine in 3',5'-deacetylated form of high purity represented by the formula [10].

The temperature condition is generally −20 to +100° C., preferably −10 to +80° C., particularly more preferably 0 to +60° C. In the case of using the reaction under a temperature condition that is higher than boiling point of the used base, it is possible to use a pressure-proof reaction vessel.

Although the reaction time is generally 0.1-120 hr, it varies depending on the reaction conditions. Therefore, it is preferable to terminate the reaction after confirming that the raw material has almost been consumed by tracing the progress condition of the reaction by an analytical means such as thin-layer chromatography, liquid chromatography, and NMR.

The post treatment is not particularly limited. In general, the acid catalyst and the base, which have been used excessively, and the reaction solvent in the reaction-terminated liquid are concentrated. With this, it is possible to recover a white-color crystalline powder of high purity with good yield. According to need, it is possible to obtain the target 2'-deoxy-2'-fluorouridine represented by the formula [9] with a higher chemical purity by subjecting the white-color crystalline powder of high purity to a purification operation such as activated carbon treatment or recrystallization. In particular, recrystallization purification can efficiently remove acetamide, which is produced as a by-product in the case of using ammonia as the base. The present recrystallization purification can similarly be conducted, based on the recrystallization purification step of the fifth step. In this case, it is conducted by regarding crude crystals of 2'-deoxy-2'-fluorouridine in 3',5'-diacetylated form represented by the formula [10] as a high-purity, white-color, crystalline powder of 2'-deoxy-2'-fluorouridine represented by the formula [9].

In the following, although embodiments of the present invention are explained by examples, the present invention is not limited to these examples.

REFERENTIAL EXAMPLE 1

Production of the Starting Material, 1-β-D-Arabinofuranosyluracil in 3',5'-Hydroxyl-Protected Form A glass reaction vessel was charged with 50.00 g (0.221 mol, 1 eq) of 2,2'-anhydrouridine represented by the following formula,

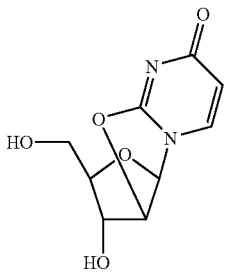

320 ml of N,N-dimethylformamide, and 129.08 g (1.534 mol, 6.94 eq.) of 3,4-dihydro-2H-pyrane, followed by cooling to 0° C., then adding 25.60 g (0.135 mol, 0.61 eq.) of p-toluenesulfuonic acid monohydrate, and then stirring at room temperature for 18 hours and 50 minutes. By an analysis of the reaction-terminated liquid with liquid chromatography, there was confirmed the production of 2,2'-anhydrouridine in 3',5'-hydroxyl-protected form, with a conversion of 98.1%, represented with the following formula.

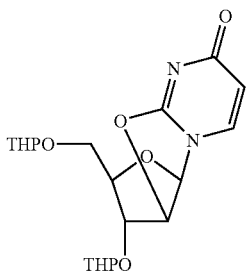

To the reaction-terminated liquid, 13.07 g (0.129 mol, 0.58 eq.) of triethylamine were added, followed by cooling to 0° C., then adding 230 ml (0.460 mol, 2.08 eq.) of 2N sodium hydroxide aqueous solution, and then stirring at room temperature for 2 hours and 15 minutes. By an analysis of the reaction-terminated liquid with liquid chromatography, there was confirmed the production of 1-β-D-arabinofuranosyluracil in 3',5'-hydroxyl-protected form, with a conversion of 98.7%, represented with the following formula.

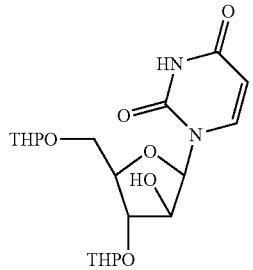

To the reaction-terminated liquid, 29.37 g (0.489 mol, 2.21 eq.) of acetic acid and 200 ml of water were added, followed by extraction with 250 ml of ethyl acetate. The recovered aqueous layer was extracted two times with 150 ml of ethyl acetate. The recovered organic layer was dried with anhydrous sodium sulfate, followed by filtration, concentration under vacuum, and azeotropy three times with small amounts of toluene, thereby obtaining 196.12 g of a crude product of 1-β-D-arabinofuranosyluracil in 3',5'-hydroxyl-protected form represented by the above formula. The recovered amount of the crude product exceeded the weight (91.15 g) of the theoretical yield.

EXAMPLE 1

Trifluoromethanesulfonylation Step of the First Step and Fluorination Step of the Second Step A pressure-proof reaction vessel made of SUS was charged with 142.90 g (0.145 mol, 1 eq.) of the crude product of 1-β-D-arabinofuranosyluracil in 3',5'-hydroxyl-protected form, produced in [Referential Example 1], represented by the following formula,

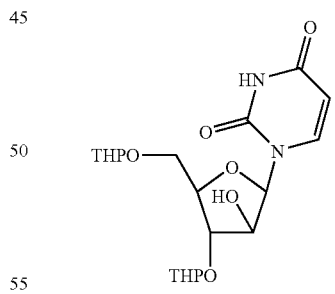

290 ml of N,N-dimethylformamide, and 87.12 g (0.861 mol, 5.94 eq.) of triethylamine, followed by cooling the inside temperature to −54° C., then adding 45.00 g (0.296 mol, 2.04 eq.) of trifluoromethanesulfonyl fluoride, and then increasing the temperature to −20° C. by spending 2 hours and 30 minutes with stirring. The reaction-terminated liquid was analyzed with $^{19}$F-NMR. With this, there was confirmed the production of a 2'-triflate form represented by the following formula

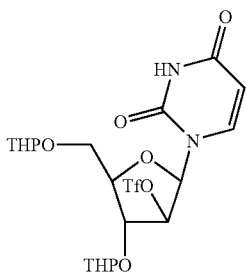

¹⁹F-NMR spectrum of the 2'-triflate form is shown in the following.

¹⁹F-NMR (standard substance: $C_6F_6$, solvent: $CDCl_3$), δppm: 87.06, 87.09, 87.17, 87.20

To the reaction-terminated liquid, 118.00 g (0.732 mol, 5.05 eq.) of $(C_2H_5)_3N\cdot 3HF$ were added at −20° C., followed by stirring at room temperature for 62 hours and 45 minutes. By an analysis of the reaction-terminated liquid by liquid chromatography, there was confirmed the production of 2'-deoxy-2'-fluorouridine in 3',5'-hydroxyl-protected form, with a conversion of >99%, represented by the following formula.

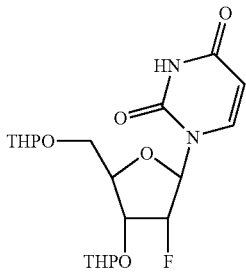

To the reaction-terminated liquid, a sodium hydrogencarbonate aqueous solution was added, followed by extraction with ethyl acetate. The recovered aqueous layer was further extracted with ethyl acetate. The recovered organic layer was dried with anhydrous sodium sulfate, followed by filtration, and concentration under vacuum, thereby obtaining 177.18 g of a crude product of 2'-deoxy-2'-fluorouridine in 3',5'-hydroxyl-protected form represented by the above formula. The recovered amount of the crude product exceeded the weight (60.09 g) of the theoretical yield. ¹⁹F-NMR spectrum of 2'-deoxy-2'-fluorouridine in 3',5'-hydroxyl-protected form is shown in the following.

¹⁹F-NMR (standard substance: $C_6F_6$, solvent: $CDCl_3$), δppm: −43.13 (dt, 51.9 Hz, 15.4 Hz), −42.50 (dt, 51.5 Hz, 15.4 Hz), −37.62 (dt, 51.5 Hz, 15.0 Hz), −37.55 (dt, 51.9 Hz, 15.0 Hz).

EXAMPLE 2

Deprotecting Step of the Third Step and Acetylating Step of the Fourth Step

A glass reaction vessel was charged with 177.18 g (0.145 mol, 1 eq.) of the crude product of 2'-deoxy-2'-fluorouridine in 3',5'-hydroxyl-protected form, produced by Example 1, represented by the following formula,

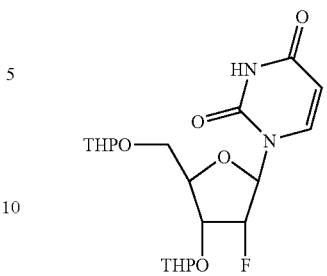

150 ml of methanol, and 13.80 g (0.073 mol, 0.50 eq.) of p-toluenesulfonic acid monohydrate, followed by stirring at room temperature for 16 hours and 30 minutes. By an analysis of the reaction-terminated liquid by liquid chromatography, there was confirmed the production of 2'-deoxy-2'-fluorouridine, with a conversion of 99.0%, represented by the following formula.

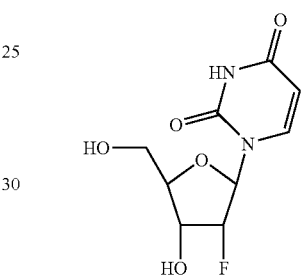

To the reaction-terminated liquid, 6.88 g (0.087 mol, 0.60 eq.) of pyridine were added, followed by concentration under vacuum, thereby obtaining a crude product of 2'-deoxy-2'-fluorouridine represented by the above formula.

The total amount of the crude product was added to a glass reaction vessel, followed by cooling to 0° C., adding 68.46 g (0.865 mol, 5.97 eq.) of pyridine and 54.10 g (0.530 mol, 3.66 eq.) of anhydrous acetic acid, and stirring at room temperature for 19 hours 10 minutes. By an analysis of the reaction-terminated liquid by liquid chromatography, there was confirmed the production of 2'-deoxy-2'-fluorouridine in 3',5'-diacetylated form, with a conversion of >99%, represented by the following formula

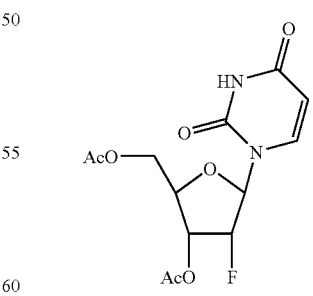

The reaction-terminated liquid was concentrated under reduced pressure at 50° C., followed by adding 80 ml of water to the concentration residue, filtration of the precipitated crystals, washing with 20 ml of ethyl acetate, and vacuum drying, thereby obtaining 58.00 g of crude crystals of 2'-deoxy-2'-fluorouridine in 3',5'-diacetylated form represented by the above formula. The recovered amount of the crude crystals exceeded the weight (47.89 g) of the theoretical yield. By an analysis of the crude crystals by liquid chromatography, HPLC purity was 90.17%. $^1$H, $^{19}$F-NMR spectra of 2'-deoxy-2'-fluorouridine in 3',5'-diacetylated form are shown in the following.

$^1$H-NMR (standard substance: TMS, solvent: DMSO-D$_6$), δppm: 1.96 (s,3H), 2.03 (s,3H), 4.08 (dd, 5.6 Hz, 12.0 Hz, 1H), 4.19 (ddd, 2.4 Hz, 5.6 Hz, 8.0 Hz, 1H), 4.26 (dd, 2.4 Hz, 12.0 Hz, 1H), 5.18 (ddd, 5.2 Hz, 8.0 Hz, 17.6 Hz, 1H), 5.46 (ddd, 2.0 Hz, 5.2 Hz, 52.4 Hz, 1H), 5.61 (d, 8.0 Hz, 1H), 5.79 (dd, 2.0 Hz, 22.6 Hz, 1H), 7.64 (d, 8.0 Hz, 1H), 11.41 (br, 1H). $^{19}$F-NMR (standard substance: C$_6$F$_6$, solvent: DMSO-D$_6$), δppm: −35.34 (dt, 51.9 Hz, 21.4 Hz).

EXAMPLE 3

Recrystallization Purification Step of the Fifth Step

A glass reaction vessel was charged with 58.00 g of crude crystals of 2'-deoxy-2'-fluorouridine in 3',5'-diacetylated form, produced by Example 2, represented by the following formula,

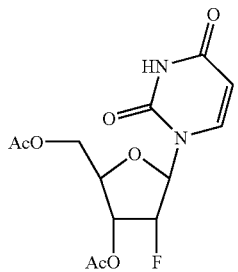

330 ml of methanol and 120 ml of water, followed by heating dissolution under reflux condition and then decreasing the temperature to room temperature with stirring. The precipitated crystals were filtered, followed by washing with methanol and vacuum drying, thereby obtaining 33.48 g of a high purity product of 2'-deoxy-2'-fluorouridine in 3',5'-diacetylated form. The total yield from the crude product of 1-β-D-arabinofuranosyluracil in 3',5'-hydroxyl-protected form to the high purity product of 2'-deoxy-2'-fluorouridine in 3',5'-diacetylated form was 70% (the weight of theoretical yield: 47.89 g). By an analysis of the high purity product by liquid chromatography, HPLC purity was 99.49%.

Again, 33.48 g of the high purity product were subjected to a similar recrystallization purification from 200 ml of methanol and 100 ml of water, thereby obtaining 31.51 g of 2'-deoxy-2'-fluorouridine in 3',5'-diacetylated form represented by the above formula of higher purity. Recovery of the second recrystallization purification was 94%. The total yield from the crude product of 1-β-D-arabinofuranosyluracil in 3',5'-hydroxyl-protected form to the twice recrystallized product of 2'-deoxy-2'-fluorouridine in 3',5'-diacetylated form was 66% (the weight of theoretical yield: 47.89 g). By an analysis of the twice-crystallized product by liquid chromatography, HPLC purity was 99.95%.

EXAMPLE 4

Deacetylation Step of the Sixth Step

A pressure-proof reaction vessel made of SUS was charged with 5.00 g (15.14 mmol, 1 eq.) of the twice-recrystallized product of 2'-deoxy-2'-fluorouridine in 3',5'-diacetylated form, produced by Example 3 and represented by the following formula,

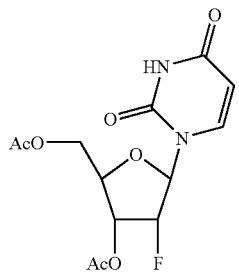

50 ml of methanol, and 12.89 g (756.90 mmol, 49.99 eq.) of ammonia, followed by stirring at room temperature for 6 hours and 30 minutes. By an analysis of the reaction-terminated liquid with liquid chromatography, there was confirmed the production of 2'-deoxy-2'-fluorouridine, with a conversion of 99.9%, represented by the following formula.

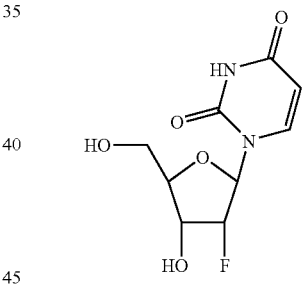

The reaction-terminated liquid was concentrated under reduced pressure, thereby obtaining 6.77 g of a high-purity, white-color, crystalline powder. A glass reaction vessel was charged with 6.77 g of the high-purity, white-color, crystalline powder, 70 ml of i-propanol, and 3 ml of n-heptane, followed by heating dissolution under reflux condition and then decreasing the temperature to room temperature with stirring. The precipitated crystals were filtered, followed by washing with i-propanol and vacuum drying, thereby obtaining 3.10 g of a higher-purity, white-color, crystalline powder of 2'-deoxy-2'-fluorouridine represented by the above formula. The total yield of the deacetylation reaction and the recrystallization purification was 83%. The converted total yield from the crude product of 1-β-D-arabinofuranosyluracil in 3',5'-hydroxyl-protected form to the recrystallized product of 2'-deoxy-2'-fluorouridine was 55%. By an analysis of the recrystallized product with liquid chromatography, HPLC purity was 99.84%. $^1$H, $^{19}$F-NMR spectra of 2'-deoxy-2'-fluorouridine are shown in the following.

$^1$H-NMR (standard substance: TMS, solvent: DMSO-D$_6$), δppm: 3.57 (d, 12.8 Hz, 1H), 3.75 (d, 12.8 Hz, 1H), 3.86 (d, 7.6 Hz, 1H), 4.13 (ddd, 4.4 Hz, 7.6 Hz, 20.8 Hz, 1H), 5.02 (ddd, 2.0 Hz, 4.4 Hz, 53.2 Hz, 1H), 5.20 (br-t, 1H), 5.61 (br, 1H), 5.61 (dd, 2.0 Hz, 8.0 Hz, 1H), 5.89 (dd, 2.0 Hz, 17.6 Hz, 1H), 7.91 (d, 8.0 Hz, 1H), 11.38 (br-d, 1H). $^{19}$F-NMR (standard substance: C$_6$F$_6$, solvent: DMSO-D$_6$), δppm: −39.77 (dt, 51.5 Hz, 18.4 Hz).

EXAMPLE 5

Deacetylation Step of the Sixth Step

A glass reaction vessel was charged with 199.00 g (0.603 mol, 1 eq., HPLC purity: 99.60%) of a high purity product of 2'-deoxy-2'-fluorouridine in 3',5'-diacetylated form, similarly produced based on Referential Example 1 and Example 1 to Example 3 and represented by the following formula,

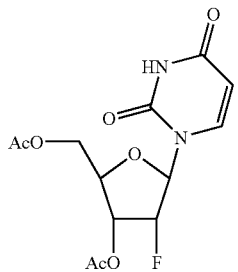

and 4020 ml of methanol, followed by stirring at 60° C. for 1 hr. The internal temperature was cooled to 55° C., followed by addition of 200 ml (0.422 mol, 0.70 eq.) of 2.11M hydrochloric acid methanol and stirring at 45° C. for 19 hours. By an analysis of the reaction-terminated liquid with liquid chromatography, there was confirmed the production of 2'-deoxy-2'-fluorouridine, with a conversion of >99.5%, represented by the following formula.

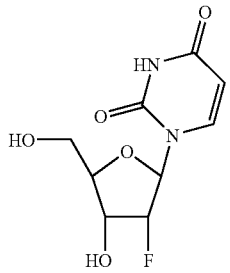

The reaction-terminated liquid was filtered and concentrated under reduced pressure, thereby obtaining 196.38 g of a high-purity, white-color, crystalline powder. A glass reaction vessel was charged with 196.38 g of the high-purity, white-color, crystalline powder, 900 ml of i-propanol, and 300 ml of n-heptane, followed by a heating stirring washing at 50° C. for 30 minutes and decreasing the temperature to room temperature. The precipitated crystals were filtered, followed by vacuum drying, thereby obtaining 137.51 g of a higher-purity, white-color, crystalline powder of 2'-deoxy-2'-fluorouridine represented by the above formula. The total yield of the deacetylation reaction and the heating stirring washing was 93%. By an analysis of the heating stirring washing product with liquid chromatography, HPLC purity was 99.50%. $^1$H, $^{19}$F-NMR spectra of 2'-deoxy-2'-fluorouridine were similar to those shown in Example 4.

REFERENTIAL EXAMPLE 2

Production of the Starting Material, 1-β-D-Arabinofuranosyluracil in 3',5'-hydroxyl-protected Form A glass reaction vessel was charged with 700 ml of N,N-dimethylformamide and 235.00 g (2.794 mol, 4.00 eq.) of 3,4-dihydro-2H-pyrane, followed by cooling to 0° C., addition of 80.00 g (0.421 mol, 0.60 eq.) of p-toluenesulfonic acid monohydrate, at the same temperature addition of 158.00 g (0.699 mol, 1 eq.) of 2,2'-anhydrouridine represented by the following formula,

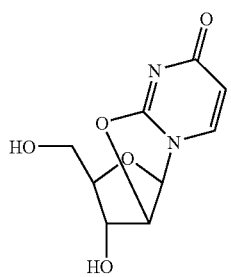

and stirring at room temperature for 15 hours and 35 minutes. By an analysis of the reaction-terminated liquid with liquid chromatography, there was confirmed the production of 2,2'-anhydrouridine in 3',5'-hydroxyl-protected form, with a conversion of 99.3%, represented with the following formula.

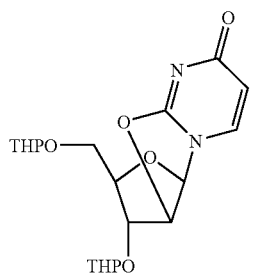

The reaction-terminated liquid was cooled to 0° C., followed by adding 360 ml (1.800 mol, 2.58 eq.) of 5N sodium hydroxide aqueous solution and stirring at room temperature for 1 hour and 55 minutes. By an analysis of the reaction-terminated liquid with liquid chromatography, there was confirmed the production of 1-β-D-arabinofuranosyluracil in 3',5'-hydroxyl-protected form, with a conversion of 98.7%, represented by the following formula

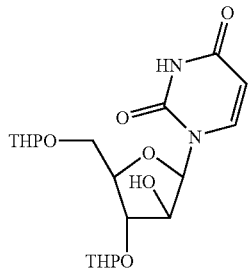

To the reaction-terminated liquid, 89.17 g (1.485 mol, 2.12 eq.) of acetic acid were added, followed by extraction with 450 ml of ethyl acetate. The recovered aqueous layer was further extracted with 200 ml of ethyl acetate. The recovered organic layer was concentrated under reduced pressure, thereby obtaining 479.94 g of a crude product of 1-β-D-arabinofuranosyluracil in 3',5'-hydroxyl-protected form. The recovered amount of the crude product exceeded the weight (288.29 g) of the theoretical yield.

EXAMPLE 6

Trifluoromethanesulfonylation Step of the First Step and Fluorination Step of the Second Step A reaction vessel made of SUS was charged with 479.94 g (0.699 mol, 1 eq.) of a crude product of 1-β-D-arabinofuranosyluracil in 3',5'-hydroxyl-protected form, produced by [Referential Example 2] and represented by the following formula,

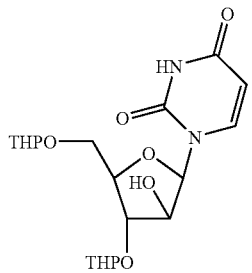

880 ml of acetonitrile and 428.34 g (4.233 mol, 6.06 eq.) of triethylamine, followed by cooling to 0° C., addition of 451.00 g (2.797 mol, 4.00 eq.) of $(C_2H_5)_3N \cdot 3HF$, a further cooling, addition of 191.00 g (1.256 mol, 1.80 eq.) of trifluoromethanesulfonyl fluoride at an internal temperature of −23 to −45° C., and stirring at room temperature for 110 hours and 55 minutes. By an analysis of the reaction-terminated liquid with liquid chromatography, there was confirmed the production of 2'-deoxy-2'-fluorouridine in 3',5'-hydroxyl-protected form, with a conversion of 99.8%, represented by the following formula.

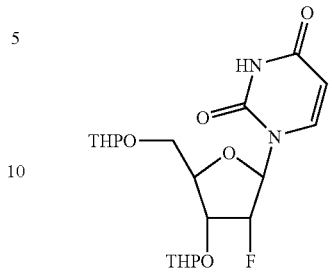

To a two-phase system solution prepared by dissolving 350.00 g (2.532 mol, 3.62 eq.) of potassium carbonate in 3000 ml of water and then adding 800 ml of ethyl acetate, the reaction-terminated liquid was added with stirring, followed by extraction with ethyl acetate. The recovered aqueous layer was further extracted with 500 ml of ethyl acetate. The recovered organic layer was concentrated under reduced pressure, thereby obtaining 794.54 g of a crude product of 2'-deoxy-2'-fluorouridine in 3',5'-hydroxyl-protected form represented by the above formula. The recovered amount of the crude product exceeded the weight (289.69 g) of the theoretical yield. $^{19}$F-NMR spectrum of 2'-deoxy-2'-fluorouridine in 3',5'-hydroxyl-protected form was similar to that shown in [Example 1].

EXAMPLE 7

Deprotection Step of the Third Step and Acetylation Step of the Fourth Step

A glass reaction vessel was charged with 794.54 g (defined as 0.699 mol, 1 eq.) of the crude product of 2'-deoxy-2'-fluorouridine in 3',5'-hydroxyl-protected form, produced by [Example 6] and represented by the following formula,

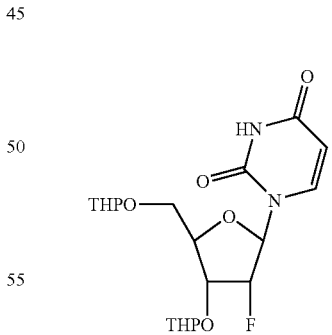

700 ml of methanol, and 66.60 g (0.350 mol, 0.50 eq.) of p-toluenesulfonic acid monohydrate, followed by stirring at room temperature for 40 hours and 30 minutes. By an analysis of the reaction-terminated liquid with liquid chromatography, there was confirmed the production of 2'-deoxy-2'-fluorouridine, with a conversion of 100%, represented by the following formula.

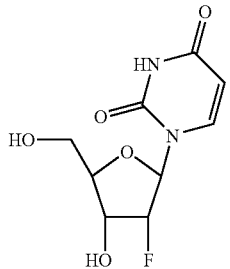

To the reaction-terminated liquid, 88.02 g (1.113 mol, 1.59 eq.) of pyridine were added, followed by concentration under reduced pressure, thereby obtaining a crude product of 2'-deoxy-2'-fluorouridine represented by the above formula.

The total amount of the crude product was added to a glass reaction vessel, followed by adding 489.00 g (6.182 mol, 8.84 eq.) of pyridine, cooling to 0° C., addition of 541.00 g (5.299 mol, 7.58 eq.) of anhydrous acetic acid, and stirring at room temperature for 40 minutes. By an analysis of the reaction-terminated liquid with liquid chromatography, there was confirmed the production of 2'-deoxy-2'-fluorouridine in 3',5'-diacetylated form, with a conversion of 96.6%, represented by the following formula.

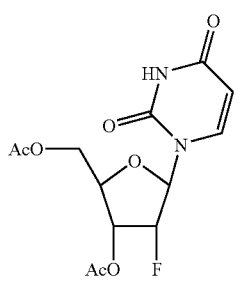

The reaction-terminated liquid was concentrated under reduced pressure, followed by cooling the concentration residue to 0° C., addition of 160 ml of water and 160 ml of ethyl acetate, stirring at the same temperature, filtration of the precipitated crystals, and vacuum drying, thereby obtaining 175.36 g of crude crystals of 2'-deoxy-2'-fluorouridine in 3',5'-diacetylated form. The total yield from 2,2'-anhydrouridine to the crude crystals of 2'-deoxy-2'-fluorouridine in 3',5'-diacetylated form was 76% (the weight of the theoretical yield: 230.86 g). By an analysis of the crude crystals with liquid chromatography, HPLC purity was 96.90%. $^1$H, $^{19}$F-NMR spectra of 2'-deoxy-2'-fluorouridine in 3',5'-diacetylated form were similar to those shown in [Example 2].

EXAMPLE 8

Recrystallization Purification Step of the Fifth Step

A glass reaction vessel was charged with 175.36 g of crude crystals of 2'-deoxy-2'-fluorouridine in 3',5'-diacetylated form, produced by [Example 7], represented by the following formula

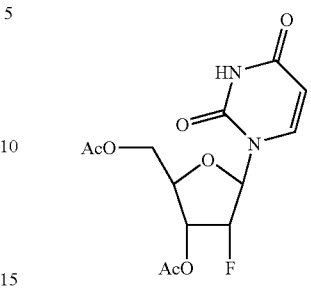

700 ml of acetonitrile, followed by a heating dissolution under reflux condition and then decreasing the temperature to room temperature with stirring. The precipitated crystals were filtered and vacuum dried, thereby obtaining 143.22 g of a high purity product of 2'-deoxy-2'-fluorouridine in 3',5'-diacetylated form. The total yield from 2,2'-anhydrouridine to the high purity product of 2'-deoxy-2'-fluorouridine in 3',5'-diacetylated form was 62% (the weight of theoretical yield: 230.86 g). By an analysis of the high purity product with liquid chromatography, HPLC purity was 99.80%.

EXAMPLE 9

Trifluoromethanesulfonylation Step of the First Step and Fluorination Step of the Second Step A glass reaction vessel was charged with 0.412 g (defined as 0.999 mmol, 1 eq.) of a crude product of 1-β-D-arabinofuranosyluracil in 3',5'-hydroxyl-protected form, similarly produced based on [Referential Example 1] and represented by the following formula,

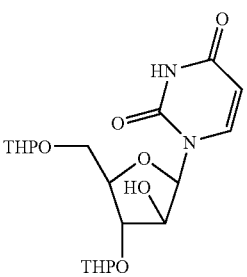

5 ml of N,N-dimethylformamide, and 0.799 g (7.896 mmol, 7.90 eq.) of triethylamine, followed by cooling to −78° C., addition of 0.335 g (1.187 mmol, 1.19 eq.) of trifluoromethanesulfonic acid anhydride, and stirring at −78° C. for 10 minutes.

By an analysis of the reaction-terminated liquid with $^{19}$F-NMR, there was confirmed the production of a 2'-triflate form represented by the following formula.

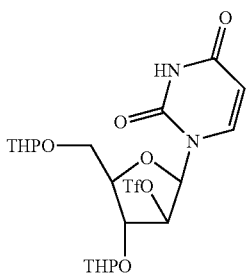

¹⁹F-NMR spectrum of the 2'-triflate form was similar to that shown in [Example 1].

To the reaction-terminated liquid, 0.2 ml of "a complex (~10 mol % C₅H₅N. ~90 mol % HF) comprising ~30% (~10 mol %) of pyridine and ~70% (~90 mol %) of hydrofluoric acid" were added, followed by stirring at room temperature for 3 hours. By an analysis of the reaction-terminated liquid with liquid chromatography, there was confirmed the production of 2'-deoxy-2'-fluorouridine in 3',5'-hydroxyl-protected form, with a conversion of 62%, represented by the following formula.

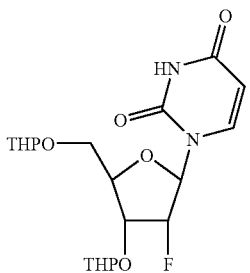

To the reaction-terminated liquid, saturated sodium hydrogencarbonate aqueous solution was added, followed by extraction with ethyl acetate. The recovered organic layer was dried with anhydrous sodium sulfate, filtered, and concentrated under reduced pressure, thereby obtaining 0.816 g of a crude product of 2'-deoxy-2'-fluorouridine in 3',5'-hydroxyl-protected form represented by the above formula. The recovered amount of the crude product exceeded the weight (0.414 g) of the theoretical yield. Thus, it was subjected to a purification operation by column chromatography (silica gel/ethyl acetate n-hexane=1:1), and the precise weight of the purified product was measured, thereby obtaining 0.324 g of the purified product. The total yield from the crude product of 1-β-D-arabinofuranosyluracil in 3',5'-hydroxyl-protected form to the purified product of 2'-deoxy-2'-fluorouridine in 3',5'-hydroxyl-protected form was 78%. ¹⁹F-NMR spectrum of 2'-deoxy-2'-fluorouridine in 3',5'-hydroxyl-protected form was similar to that shown in [Example 1].

The invention claimed is:

1. A process for producing a hydroxyl-protected 2'-deoxy-2'-fluorouridine compound represented by formula [4],

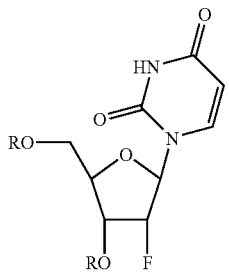

[4]

wherein R represents a hydroxyl-protecting group, by reacting 1-β-D-arabinofuranosyluracil in 3',5'-hydroxyl-protected form, represented by formula [1],

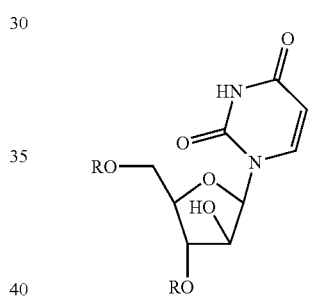

[1]

wherein R has the meaning given above, with a trifluoromethanesulfonylating agent represented by formula [2], $$CF_3SO_2X \quad [2]$$

wherein X represents an F atom, Cl atom or $CF_3SO_3$ group, in the presence of an organic base, to convert it to a 2'-triflate compound represented by formula [3],

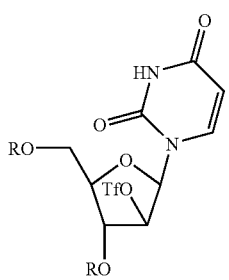

[3]

wherein R has the meaning given above, and T' represents a $CF_3SO_2$ group, followed by reacting with a fluorinating agent comprising a salt or complex comprising an organic base and hydrofluoric acid.

2. A process for producing a hydroxyl-protected 2'-deoxy-2'-fluorouridine compound represented by formula [4],

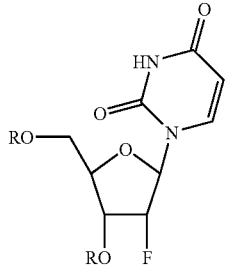

[4]

wherein R represents a hydroxyl-protecting group, by reacting 1-β-D-arabinofuranosyluracil in 3',5'-hydroxyl-protected form, represented by formula [1],

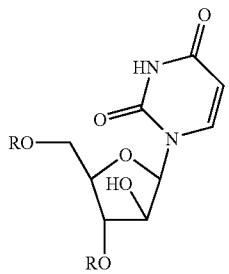

[1]

wherein R has the meaning given above, with a trifluoromethanesulfonylating agent represented by formula [5],

 [5]

in the presence of triethylamine, to convert it to a 2'-triflate compound represented by formula [3],

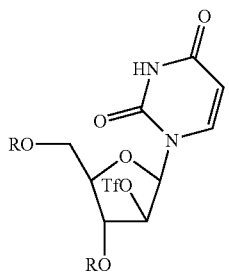

[3]

wherein R has the meaning given above, and Tf represents a $CF_3SO_2$ group, followed by reacting with a fluorinating agent comprising a salt or complex comprising triethylamine and hydrofluoric acid.

3. A process for producing a hydroxyl-protected 2'-deoxy-2'-fluorouridine compound represented by formula [8],

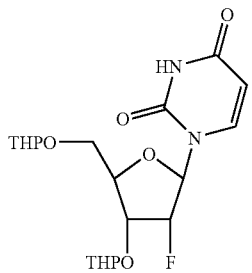

[8]

wherein THP represents a tetrahydropyranyl group, by reacting 1-β-D-arabinofuranosyluracil in 3',5'-hydroxyl-protected form, represented by formula [6],

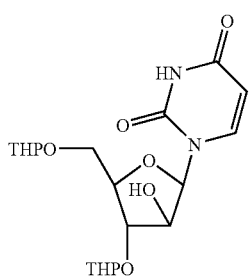

[6]

wherein THP has the meaning given above, with a trifluoromethanesulfonylating agent represented by formula [5],

 [5]

in the presence of triethylamine, to convert it to a 2'-triflate compound represented by formula [7],

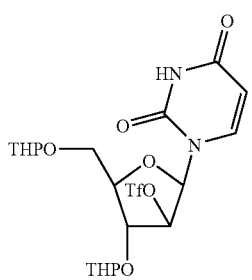

[7]

wherein THP has the meaning given above, and Tf represents a $CF_3SO_2$ group, followed by reacting with a fluorinating agent comprising a salt or complex comprising triethylamine and hydrofluoric acid.

4. A process for producing 2'-deoxy-2'-fluorouridine represented by formula [9],

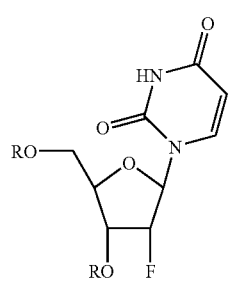

acid, to convert it to a hydroxyl-protected 2'-deoxy-2'-fluorouridine compound represented by formula [4],

[4]

wherein R has the meaning given above, and (c) reacting the hydroxyl-protected 2'-deoxy-2'-fluorouridine compound represented by formula [4], with a deprotecting agent.

5. A process for purifying 2'-deoxy-2'-fluorouridine represented by formula [9],

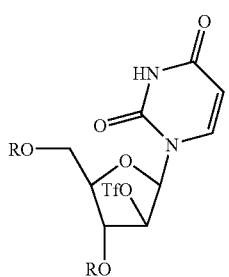

the process comprising the steps of:

(a) reacting 1-β-D-arabinofuranosyluracil in 3',5'-hydroxyl-protected form, represented by formula [1],

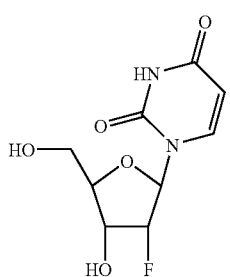

[1]

wherein R represents a hydroxyl-protecting group, with a trifluoromethanesulfonylating agent represented by formula [2],

CF$_3$SO$_2$X [2]

wherein X represents an F atom, Cl atom or CF$_3$SO$_3$ group, in the presence of an organic base, to convert it to a 2'-triflate compound represented by formula [3],

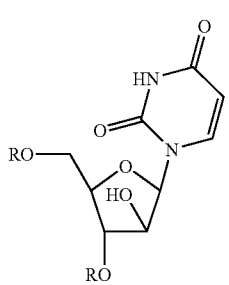

[3]

wherein R has the meaning given above, and Tf represents a CF$_3$SO$_2$ group, (b) reacting the 2'-triflate compound represented by formula [3], with a fluorinating agent comprising a salt or complex comprising an organic base and hydrofluoric

[9]

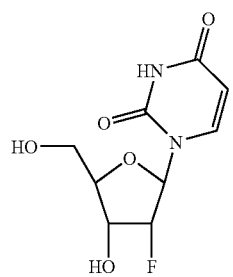

comprising reacting 2'-deoxy-2'-fluorouridine represented by formula [9],

[9]

with an acetylating agent in the presence of an organic base, to convert it to 3',5'-diacetylated 2'-deoxy-2'-fluorouridine represented by formula [10],

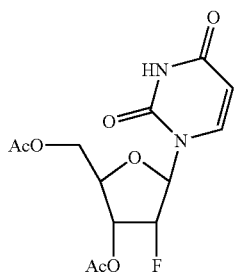

[10]

wherein Ac represents an acetyl group, followed by a recrystallization purification of the 3',5'-diacetylated 2'-deoxy-2-fluorouridine and then reacting with a deacetylating agent.

6. A process for purifying 2'-deoxy-2'-fluorouridine represented by formula [9],

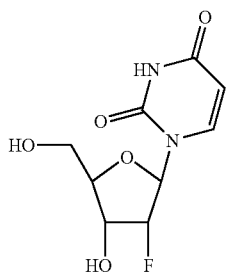

[9]

the process comprising the steps of:

(a) reacting 1-β-D-arabinofuranosyluracil in 3',5'-hydroxyl-protected form, represented by formula [1],

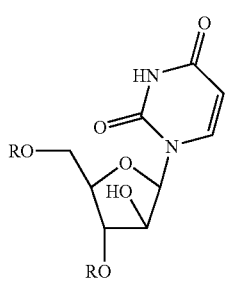

[1]

wherein R represents a hydroxyl-protecting group, with a trifluoromethanesulfonylating agent represented by formula [2], $$CF_3SO_2X$$ [2]

wherein X represents an F atom, Cl atom or $CF_3SO_3$ group, in the presence of an organic base, to convert it to a 2'-triflate compound represented by formula [3],

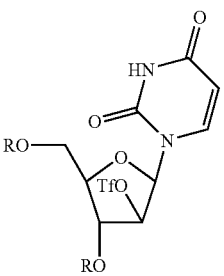

[3]

wherein R has the meaning given above, and Tf represents a $CF_3SO_2$ group, (b) reacting the 2'-triflate compound represented by formula [3], with a fluorinating agent comprising a salt or complex comprising an organic base and hydrofluoric acid, to convert it to a hydroxyl-protected 2'-deoxy-2'-fluorouridine compound represented by formula [4],

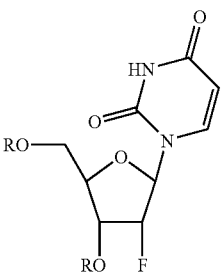

[4]

wherein R has the meaning given above, (c) reacting the hydroxyl-protected 2'-deoxy-2'-fluorouridine compound represented by formula [4], with a deprotecting agent, to convert it to 2'-deoxy-2'-fluorouridine represented by formula [9],

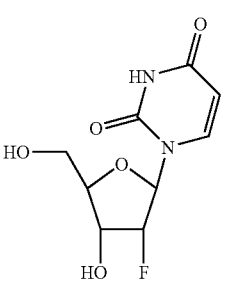

[9]

and (d) reacting the 2'-deoxy-2t-fluorouridine represented by formula [9], with an acetylating agent in the presence of an organic base, to convert it to 3',5'-diacetylated 2'-deoxy-2'-fluorouridine represented by formula [10],

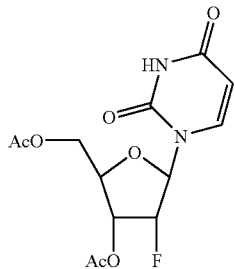

wherein Ac represents an acetyl group, followed by a recrystallization purification of the 3',5'-diacetylated 2'-deoxy-2'-fluorouridine and then reacting with a deacetylating agent.

7. A 2'-triflate compound represented by formula [7],

[7]

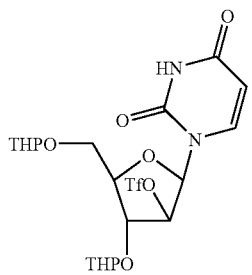

wherein THP represents a tetrahydropyranyl group, and Tf represents a CF$_3$SO$_2$ group.

8. A process for producing 2'-deoxy-2'-fluorouridine represented by formula [9],

[9]

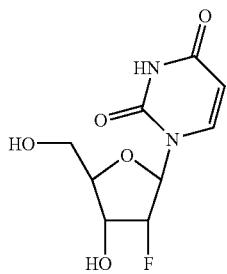

the process comprising the steps of:
(a) reacting 1-β-D-arabinofuranosyluracil in 3',5'-hydroxyl-protected form, represented by formula [1],

[1]

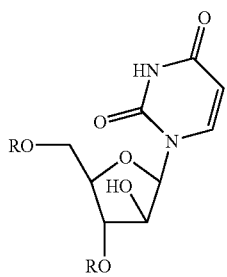

wherein R represents a hydroxyl-protecting group, with a trifluoromethanesulfonylating agent represented by formula [5],

CF$_3$SO$_2$F [5]

in the presence of triethylamine, to convert it to a 2'-triflate compound represented by formula [3],

[3]

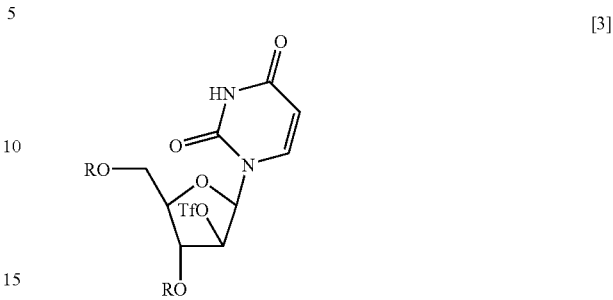

wherein R has the meaning given above, and Tf represents a CF$_3$SO$_2$ group, (b) reacting the 2'-triflate compound represented by formula [3], with a fluorinating agent comprising a salt or complex comprising triethylamine and hydrofluoric acid, to convert it to a hydroxyl-protected 2'-deoxy-2'-fluorouridine compound represented by formula [4],

[4]

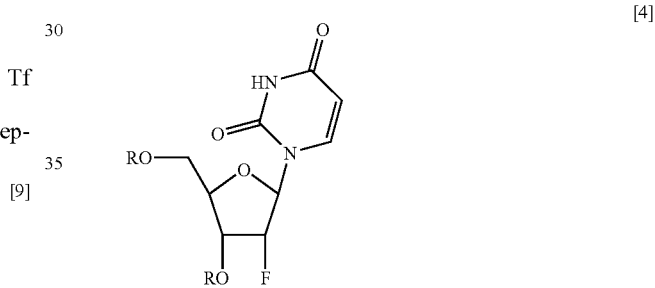

wherein R has the meaning given above, and
(c) reacting the hydroxyl-protected 2'-deoxy-2'-fluorouridine compound represented by formula [4], with a deprotecting agent.

9. A process for purifying 2'-deoxy-2'-fluorouridine represented by formula [9],

[9]

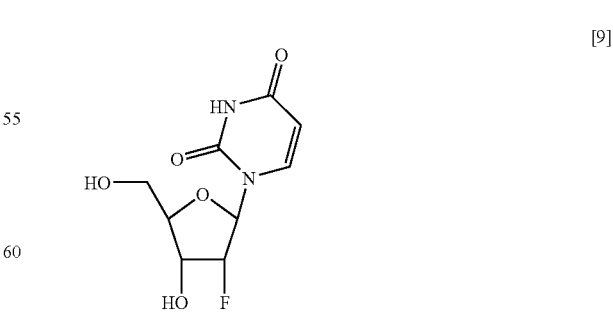

the process comprising the steps of:
(a) reacting 1-β-D-arabinofuranosyluracil in 3',5'-hydroxyl-protected form, represented by formula [1],

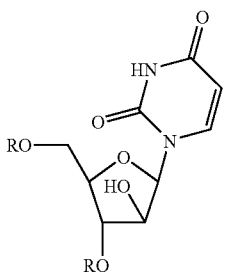
[1]

wherein R represents a hydroxyl-protecting group, with a trifluoromethanesulfonylating agent represented by formula [5],

 [5]

in the presence of triethylamine, to convert it to a 2'-triflate compound represented by formula [3],

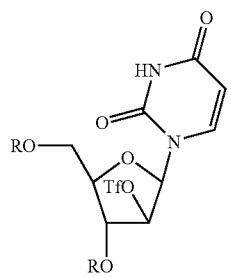
[3]

wherein R has the meaning given above, and Tf represents a $CF_3SO_2$ group, (b) reacting the 2'-triflate compound represented by formula [3], with a fluorinating agent comprising a salt or complex comprising triethylamine and hydrofluoric acid, to convert it to a hydroxyl-protected 2'-deoxy-2'-fluorouridine compound represented by formula [4],

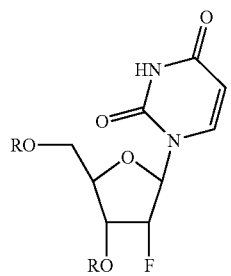
[4]

wherein R has the meaning given above, and (c) reacting the hydroxyl-protected 2'-deoxy-2'-fluorouridine compound represented by formula [4], with a deprotecting agent, to convert it to 2'-deoxy-2'-fluorouridine represented by formula [9],

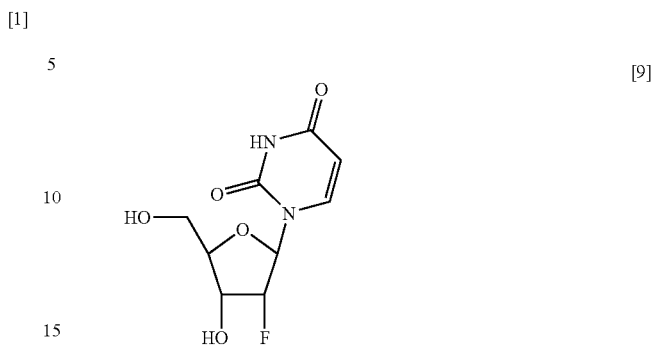
[9]

and (d) reacting the 2'-deoxy-2'-fluorouridine represented by formula [9], with an acetylating agent in the presence of an organic base, to convert it to 3',5'-diacetylated 2'-deoxy-2'-fluorouridine represented by formula [10],

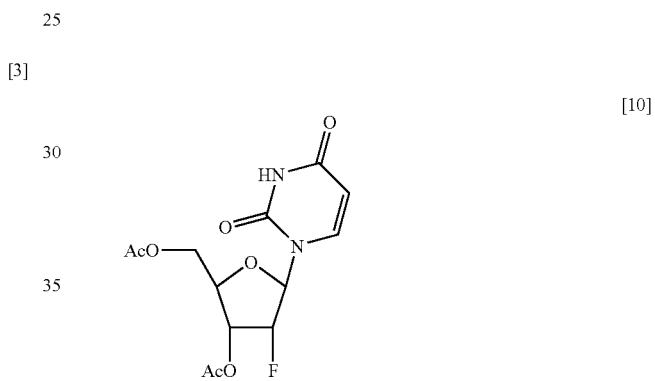
[10]

wherein Ac represents an acetyl group, followed by a recrystallization purification of the 3',5'-diacetylated 2'-deoxy-2'-fluorouridine and then reacting with a deacetylating agent.

10. A process for producing 2'-deoxy-2'-fluorouridine represented by formula [9],

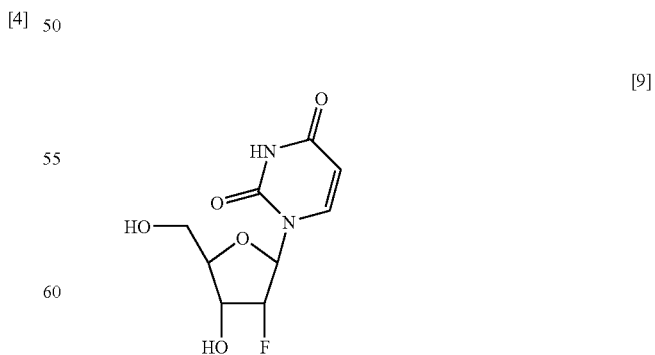
[9]

the process comprising the steps of:

(a) reacting 1-β-D-arabinofuranosyluracil in 3',5'-hydroxyl-protected form, represented by formula [6],

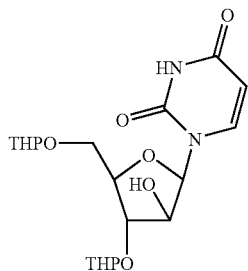
[6]

wherein THP represents a tetrahydropyranyl group, with a trifluoromethanesulfonylating agent represented by formula [5],

CF$_3$SO$_2$F  [5]

in the presence of triethylamine, to convert it to a 2'-triflate compound represented by formula [7],

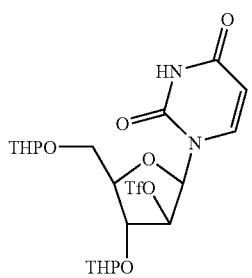
[7]

wherein THP has the meaning given above, and Tf represents a CF$_3$SO$_2$ group, (b) reacting the 2'-triflate compound represented by formula [7], with a fluorinating agent comprising a salt or complex comprising triethylamine and hydrofluoric acid, to convert it to a hydroxyl-protected 2'-deoxy-2'-fluorouridine compound represented by formula [8],

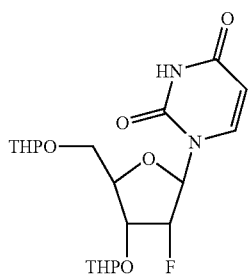
[8]

wherein THP has the meaning given above, and
(c) reacting the hydroxyl-protected 2'-deoxy-2'-fluorouridine compound represented by formula [8], with a deprotecting agent.

11. A process for purifying 2'-deoxy-2'-fluorouridine represented by formula [9],

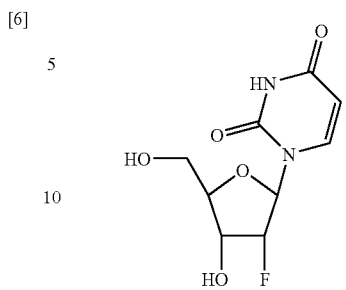
[9]

the process comprising the steps of:
(a) reacting 1-β-D-arabinofuranosyluracil in 3',5'-hydroxyl-protected form, represented by formula [6],

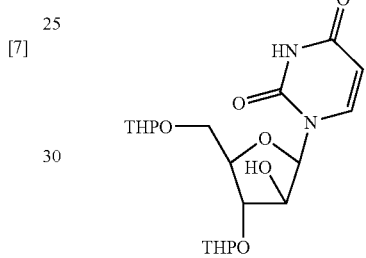
[6]

wherein THP represents a tetrahydropyranyl group, with a trifluoromethanesulfonylating agent represented by formula [5],

CF$_3$SO$_2$F  [5]

in the presence of triethylamine, to convert it to a 2'-triflate compound represented by formula [7],

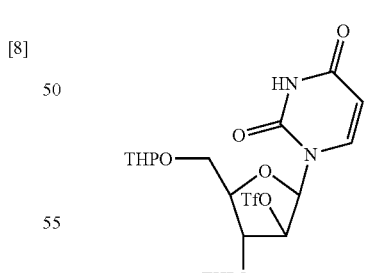
[7]

wherein THP has the meaning given above, and Tf represents a CF$_3$SO$_2$ group, (b) reacting the 2'-triflate compound represented by formula [7], with a fluorinating agent comprising a salt or complex comprising triethylamine and hydrofluoric acid, to convert it to a hydroxyl-protected 2'-deoxy-2'-fluorouridine compound represented by formula [8],

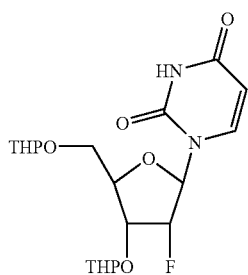

[8]

wherein THP has the meaning given above, and (c) reacting the hydroxyl-protected 2'-deoxy-2'-fluorouridine compound represented by formula [8], with a deprotecting agent, to convert it to 2'-deoxy-2'-fluorouridine represented by formula [9],

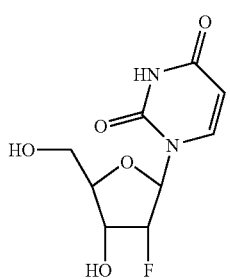

[9]

and (d) reacting the 2'-deoxy-2'-fluorouridine represented by formula [9], with an acetylating agent in the presence of an organic base, to convert it to 3',5'-diacetylated 2'-deoxy-2'-fluorouridine represented by formula [10],

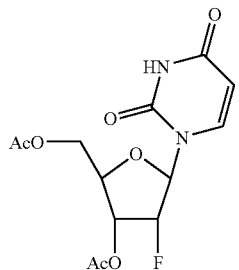

[10]

wherein Ac represents an acetyl group, followed by a recrystallization purification of the 3',5'-diacetylated 2'-deoxy-2'fluorouridine and then reacting with a deacetylating agent.

* * * * *